US011684582B2

(12) United States Patent
Eshima

(10) Patent No.: US 11,684,582 B2
(45) Date of Patent: Jun. 27, 2023

(54) METHOD FOR STABILIZING HUMIDITY-SENSITIVE PHARMACEUTICAL SUBSTANCE AND STABILIZED PREPARATION THEREOF

(71) Applicant: Delta-Fly Pharma, Inc., Tokushima (JP)

(72) Inventor: Kiyoshi Eshima, Tokushima (JP)

(73) Assignee: Delta-Fly Pharma, Inc., Tokushima (JP)

( * ) Notice: Subject to any disclaimer, the term of this patent is extended or adjusted under 35 U.S.C. 154(b) by 0 days.

(21) Appl. No.: 17/613,448

(22) PCT Filed: Mar. 31, 2021

(86) PCT No.: PCT/JP2021/013964
§ 371 (c)(1),
(2) Date: Feb. 22, 2022

(87) PCT Pub. No.: WO2022/208784
PCT Pub. Date: Oct. 6, 2022

(65) Prior Publication Data
US 2022/0313613 A1   Oct. 6, 2022

(51) Int. Cl.
*A61K 9/48* (2006.01)
*A61K 31/513* (2006.01)

(52) U.S. Cl.
CPC ............ *A61K 9/4866* (2013.01); *A61K 9/485* (2013.01); *A61K 9/4816* (2013.01); *A61K 9/4833* (2013.01); *A61K 31/513* (2013.01)

(58) Field of Classification Search
None
See application file for complete search history.

(56) References Cited

U.S. PATENT DOCUMENTS

| 2004/0202737 A1 | 10/2004 | Moura |
| 2007/0059356 A1* | 3/2007 | Almarsson ............ A61K 31/415 514/217 |
| 2010/0297194 A1* | 11/2010 | Catron ................... A61P 35/00 424/711 |
| 2012/0232103 A1 | 9/2012 | Fukushima et al. |
| 2017/0233344 A1* | 8/2017 | Nakamura ............ C07D 215/48 546/153 |
| 2018/0055845 A1 | 3/2018 | Reents et al. |

FOREIGN PATENT DOCUMENTS

| EP | 2 495 243 A1 | 9/2012 |
| JP | 2004-525124 A | 8/2004 |
| JP | 5008778 B2 | 6/2012 |
| JP | 2019-524804 A | 9/2019 |
| RU | 2503673 C2 | 9/2013 |
| WO | WO-2011/052554 A1 | 5/2011 |

OTHER PUBLICATIONS

Ajani et al.,. "Phase I study of DFP-11207, a novel chemotherapeutic agent, in patients with solid tumors by reasonable dose escalation," The Japanese Society of Medical Oncology 2016 Annual Meeting, 2016, 03-5-4.
Ajani et al., "Food Effect Study of DFP-11207, a Novel Oral Cancer Chemotherapeutic Agent, in Patients with Solid Tumors," International Oral 2 GI Tract & Hepatobiliary, Oct. 24, 2019, 900:102-1.
Ajani et al., "Phase I study of DFP-11207, a novel oral fluoropyrimidine with reasonable AUC and low Cmax and improved tolerability in patients with solid tumors," Investigational New Drugs, May 6, 2020, 38:1763-1773.
Decision to Grant a Patent dated Sep. 7, 2021 in JP 2021-535258, with English translation.
Fukushima et al., "Development of new promising antimetabolite, DFP-11207 with self-controlled toxicity in rodents," Drug Design, Development and Therapy, 2017, 11:1693-1705.
Heidelberger et al., "Experimental and Clinical Use of Fluorinated Pyrimidines in Cancer Chemotherapy," Cancer Research, Sep. 1963, 23:1226-1243.
International Search Report dated May 25, 2021 in PCT/JP2021/013964.
Ishikawa et al., "Tumor Selective Delivery of 5-Fluorouracil by Capecitabine, a New Oral Fluoropyrimidine Carbamate, in Human Cancer Xenografts," Biochemical Pharmacology, May 1, 1998, 55:1091-1097.
Shirasaka et al., "Antitumor Activity of 1 M Tegafur-0.4 M 5-Chloro-2,4-dihydroxypyridine-1 M Potassium Oxanate (S-1) against Human Colon Carcinoma Orthotopically Implanted into Nude Rats," Cancer Research, Jun. 1, 1996, 56:2602-2606.
Chen et al., "Effects of Highly Hygroscopic Excipients on the Hydrolysis of Simvastatin in Tablet at High Relative Humidity," Indian Journal of Pharmaceutical Sciences, Nov.-Dec. 2012, 74:527-534.
Chen, Yisheng, "Packaging Selection for Solid Oral Dosage Forms," Chapter 24 in Developing Solid Oral Dosage Forms, Pharmaceutical Theory and Practice, Academic Press, 2009, 563-576.
Majee et al., "HPMC as capsule shell material: Physicochemical, Pharmaceutical and Biopharmaceutical Properties," International Journal of Pharmacy and Pharmaceutical Sciences, 2017, 9(10):1-6.
Office Action and Search Report dated Jul. 18, 2022 in RU 2021139275/04(082176), with English translations.
Sari, Airaksinen, "Role of Excipients in Moisture Sorption and Physical Stability of Solid Pharmaceutical Formulations," Academic Dissertation, Division of Pharmaceutical Technology, Faculty of Pharmacy, University of Helsinki, Finland, Oct. 29, 2005, 64 pages.

(Continued)

*Primary Examiner* — Kyung S Chang
(74) *Attorney, Agent, or Firm* — Foley & Lardner LLP

(57) ABSTRACT

An object of the present invention is to provide a method for stabilizing a substance DFP-11207 sensitive to humidity and unstable at high humidity, and a stabilized preparation thereof, and more specifically, provide a capsule preparation for treating cancer, containing DFP-11207 or a pharmaceutically acceptable salt thereof and a hygroscopic agent.

11 Claims, No Drawings

(56) References Cited

OTHER PUBLICATIONS

Ajani et al., "Phase I study of DFP-11207, a novel oral 5-FU with enhanced PK and improved tolerability, in patients with solid tumors," Database EMBASE [online], May 1, 2019, Accession No. EMB-629324714, abstract, 2 pages.
Supplementary European Search Report dated Nov. 10, 2022 in EP 21834698.9.

* cited by examiner

METHOD FOR STABILIZING HUMIDITY-SENSITIVE PHARMACEUTICAL SUBSTANCE AND STABILIZED PREPARATION THEREOF

CROSS-REFERENCE TO RELATED APPLICATIONS

This application is the U.S. National Stage of PCT/JP2021/013964, filed Mar.31, 2021.

TECHNICAL FIELD

The present invention relates to a method for pharmaceutically stabilizing a pharmaceutical substance, 5-chloro-2-(3-(3-(ethoxymethyl)-5-fluoro-2,6-dioxo-1,2,3,6-tetrahydopy-rimidine-1-carbonyl)benzoyloxy)pyridine-4-yl-2,6-bis(propionyloxy)isonicotinate) (hereinafter, referred to as "DFP-11207"), which is easily decomposed under the influence of humidity due to the presence of a large number of ester bonds in a molecule, and also relates to a stabilized preparation thereof.

BACKGROUND ART

DFP-11207 is a novel derivative of 5-fluorouracil (5-FU) and a candidate substance for a peroral anti-cancer drug (Patent Literature 1, Non Patent Literature 1, Non Patent Literature 2). 5-FU has been clinically applied mostly by intravenous infusion over a week (Non Patent Literature 3). Afterwards, oral preparations such as Xeloda (Non Patent Literature 4) and TS-1 (Non Patent Literature 5) have been clinically used.

TS-1 is a combination drug consisting of three components, that is, a 5-FU derivative, tegafur (FT); gimeracil (CDHP) inhibiting in-vivo metabolic degradation by dihydropyrimidine dehydrogenase; and oteracil potassium (OXO) inhibiting orotate phosphoribosyl transferase activity. TS-1 exerts an excellent therapeutic effect; however, the components are each individually absorbed from the intestinal wall. Due to this, side effects such as bone-marrow toxicity including reduced blood platelet count are produced. For the reason, TS-1 has room for improvement.

DFP-11207 is a single compound consisting of a 5-FU derivative, 1-ethoxymethyl-5-fluorouracil (EMFU), 5-chloro 2,4-dihydroxypyridine (CDHP) inhibiting enzymatic decomposition with dihydropyrimidine dehydrogenase, and citrazinic acid (CTA) inhibiting orotate phosphoribosyl transferase activity.

When DFP-11207 and TS-1 were each individually and orally administered in an experiment using animal models, i.e., cancer-bearing nude rats for use in estimating effects on cancer patients, the "area under the curve" (AUC) of drug concentration of 5-FU derived from DFP-11207 was the same as AUC of that of 5-FU derived from TS-1; however the maximum blood concentration (Cmax) of 5-FU derived from DFP-11207 was significantly lower than Cmax of 5-FU derived from TS-1. It is commonly known that AUC of 5-FU in the blood is likely to reflect medicinal effects of 5-FU; whereas, Cmax of 5-FU in the blood is likely to reflect side effects (particularly bone-marrow toxicity such as reduced blood platelet count). In this sense, it can be said that DFP-11207 is pharmacokinetically an excellent substance in balance between medicinal effects and side effects, compared to an existing medicine, TS-1. As a result that DFP-11207 and TS-1 were each individually and orally administered in experiments using cancer-bearing nude rats (which are optimal animal models for use in estimating medicinal effects on cancer patients) and therapeutic effects of them were compared, DFP-11207 was more excellent than TS-1 (Non Patent Literature 1). Excellent safety (none of serious gastrointestinal toxicity such as diarrhea and toxicity of reduced blood platelet count were observed) of DFP-11207 was also confirmed in the phase-I trial of DFP-11207, which was carried out in the M. D. Anderson Cancer Center in U.S. with patients having a solid cancer such as colorectal cancer, gastric cancer and pancreatic cancer (Non Patent Literature 2). In the case of TS-1, it is necessary for patients to take drug holidays in order to recover from side effect; however, in the case of DFP-11207, it is not necessary to take drug holidays or control a dosage amount depending on the body-surface area of a cancer patient (Non Patent Literature 2).

CITATION LIST

Patent Literature

[Patent Literatures 1] Japanese Patent No. 5008778

Non Patent Literatures

[Non Patent Literature 1] M. Fukushima et al., Drug Design, Development and Therapy (2017): 1693-1705
[Non Patent Literature 2] J. Ajani et al., Investigational New Drugs(2020): 1763-1773
[Non Patent Literature 3] Heidelberger et al., Cancer Research (1963): 1226-1243
[Non Patent Literature 4] H. Ishitsuka et al., Biochemical Pharmacology (1998): 1091-1097
[Non Patent Literature 5] M. Fukushima et al., Cancer Research (1996): 2602-2606

SUMMARY OF INVENTION

Technical Problem

The present inventors found that DFP-11207 is a clinically excellent anti-cancer drug candidate substance but it is not easily stored for a long term because DFP-11207 is sensitive to humidity (in other words, humidity reduces stability) due to the presence of a large number of ester bonds in a molecule.

DFP-11207 is a single compound formed by linking EMFU slowly releasing 5-FU, CDHP suppressing in-vivo metabolic decomposition of 5-FU and CTA suppressing gastrointestinal serious toxicity (e.g., diarrhea) of 5-FU, via, e.g., an ester bond. When DFP-11207 is orally administered, DFP-11207 is metabolized into EMFU, CDHP and CTA in the intestinal tissue. EMFU slowly releases 5-FU in the blood and CDHP inhibits metabolic decomposition of 5-FU in the blood. Since the concentration of 5-FU in the blood is maintained in this mechanism, the anti-tumor effect of 5-FU is enhanced. Whereas, CTA mostly stays within the intestinal tissue to reduce 5-FU induced gastrointestinal toxicity.

As mentioned above, DFP-11207 is a highly functional substance because of a combination of functional substances, that is, EMFU slowly releasing 5-FU, CDHP inhibiting enzymatic decomposition of 5-FU and CTA reducing toxicity caused by 5-FU in the gastrointestinal tissue, in a molecule; however, DFP-11207 is sensitive to humidity.

An object of the present invention is to provide a method for stabilizing DFP-11207, which is a substance sensitive to humidity and unstable at high humidity, and provide a stabilized preparation thereof.

Solution to Problem

The present inventors have intensively conducted studies with a view to solving the aforementioned problems. As a result, they have found that a humidity-sensitive substance, DFP-11207, can have an improved stability and be stored for a long term in a room or a refrigerator by formulating DFP-11207 together with a hygroscopic agent into a capsule preparation, and providing the capsule preparation in a container together with a drying agent.

The present invention was attained based on these new findings and the following inventions are included.

[1] A capsule preparation for treating cancer, comprising DFP-11207 or a pharmaceutically acceptable salt thereof and a hygroscopic agent.

[2] The capsule preparation according to [1], wherein the hygroscopic agent include colloidal silicon dioxide and microcrystalline cellulose.

[3] The capsule preparation according to [1] or [2], which comprises the DFP-11207 or a pharmaceutically acceptable salt thereof in an amount of 25 to 65 wt %, the microcrystalline cellulose in an amount of 35 to 75 wt % and the colloidal silicon dioxide in an amount of 2 to 5 wt %.

[4] The capsule preparation according to any one of [1] to [3], which comprises the DFP-11207 or a pharmaceutically acceptable salt thereof in an amount of 100 mg.

[5] The capsule preparation according to any one of [1] to [4], wherein a coating base for a capsule shell thereof contains hydroxypropyl methylcellulose.

[6] The capsule preparation according to any one of [1] to [5], which has a capsule size of 2 to 00.

[7] The capsule preparation according to any one of [1] to [6], which is provided in a container together with a drying agent.

[8] A method for producing a capsule preparation for treating cancer, comprising filling a capsule shell with DFP-11207 or a pharmaceutically acceptable salt thereof and a hygroscopic agent.

[9] The method according to [8], wherein the hygroscopic agent includes colloidal silicon dioxide and microcrystalline cellulose.

[10] The method according to [8] or [9], wherein the capsule shell is filled with DFP-11207 or a pharmaceutically acceptable salt thereof in an amount of 25 to 65 wt %, microcrystalline cellulose in an amount of 35 to 75 wt % and a colloidal silicon dioxide in an amount of 2 to 5 wt %.

[11] The method according to any one of [8] to [10], wherein the capsule shell is filled with DFP-11207 or a pharmaceutically acceptable salt thereof in an amount of 100 mg.

[12] The method according to any one of [8] to [11], wherein a coating base for the capsule shell contains hydroxypropyl methylcellulose.

[13] The method according to any one of [8] to [12], wherein the capsule shell has a capsule size of 2 to 00.

[14] The method according to any one of [8] to [13], further comprising a step of providing the produced capsule preparation in a container together with a drying agent.

Advantageous Effects of Invention

According to the present invention, it is possible to provide a method for stabilizing DFP-11207, which is a substance sensitive to humidity and unstable at high humidity, and a stabilized preparation thereof. According to the present invention, DFP-11207 is a high-functional substance obtained by linking a functional substance (EMFU) slowly releasing 5-FU, a functional substance (CDHP) inhibiting a 5-FU degrading enzyme and a functional substance (CTA) suppressing 5-FU induced gastrointestinal toxicity, via e.g., an ester bond and an active amido bond, in a molecule. Since DFP-11207, is a substance sensitive to humidity and unstable, if a method for stabilizing DFP-11207 (sensitive to humidity and an unstable substance) by suppressing movement of water molecules is invented, it is possible to provide a DFP-11207 preparation that can be stored for a long term and free from problems of transport.

DESCRIPTION OF EMBODIMENTS

The present invention relates to a capsule preparation for treating cancer, containing DFP-11207 or a pharmaceutically acceptable salt thereof and a hygroscopic agent.

In the present invention, "DFP-11207" is a compound represented by the following formula 1:

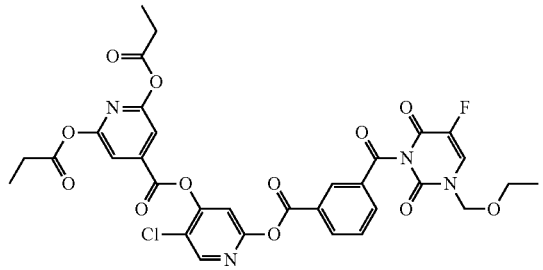

[Formula 1]

obtained by linking a 5-FU derivative, 1-ethoxymethyl-5-fluorouracil (EMFU), 5-chloro 2,4-dihydroxypyridine (CDHP) inhibiting enzymatic decomposition with dihydropyrimidine dehydrogenase, and citrazinic acid (CTA) inhibiting activity of orotate phosphoribosyl transferase, via an ester bond and an active amide bond. The "DFP-11207" to be used in the present invention may be a product produced in accordance with a method commonly known in the technical field (for example, Japanese Patent No. 5008778, M. Fukushima et al., (2017); J. Ajani et al., (2020) listed in the above) or a commercially available product.

In the present invention, the "pharmaceutically acceptable salt thereof" refers to a salt that can be administered to living bodies. Examples of the pharmaceutically acceptable salt include, but are not limited to, a hydrochloride, a sulfate, a nitrate, a phosphate, a hydrobromide, a carbonate, an acetate, a trifluoroacetate, a p-toluene sulfonate, a propionate, a tartrate, a fumarate, a malate, a maleate, a citrate, a methanesulfonate, an alkali metal salt (e.g., sodium salt, potassium salt), an alkaline earth metal salt (e.g., calcium salt), a magnesium salt and an ammonium salt.

In the present invention, the "hygroscopic agent" is not particularly limited as long as it is a pharmaceutically acceptable (more specifically, can be administered to living bodies) and it absorbs moisture. Examples of the hygroscopic agent include microcrystalline cellulose, colloidal silicon dioxide, hydroxyethyl cellulose, hydroxypropyl methylcellulose, hydroxypropyl cellulose, hydroxyethyl methyl cellulose, carboxypolymethylene, methyl cellulose, ethyl cellulose, dextran, carboxymethyl starch, starch, calcium silicate, magnesium silicate, talc, polyvinylpyrrolidone, polyvinyl alcohol, thaumatin, sodium polyphosphate, phthalic anhydride, maleic anhydride, anhydrous sodium dihydrogen phosphate and sodium metaphosphate. One or a plurality of hygroscopic agents selected from these can be used. The "hygroscopic agent" in the present invention preferably includes microcrystalline cellulose and/or colloidal silicon dioxide, and more preferably, microcrystalline cellulose and colloidal silicon dioxide are used. In the present invention, movement of water molecules can be suppressed by the content of the "hygroscopic agent", with the result that stability of DFP-11207 or a pharmaceutically acceptable salt thereof to humidity can be enhanced.

In an embodiment, the capsule preparation of the present invention may contain 25 to 65 wt % of DFP-11207 or a pharmaceutically acceptable salt thereof and 35 to 75 wt % of a hygroscopic agent.

In another embodiment, the capsule preparation of the present invention may contain 25 to 65 wt % of DFP-11207 or a pharmaceutically acceptable salt thereof, 35 to 75 wt % of microcrystalline cellulose and 2 to 5 wt % of colloidal silicon dioxide. For example, the capsule preparation of the present invention may contain 100 mg of DFP-11207 or a pharmaceutically acceptable salt thereof, 56.8 mg to 292 mg of microcrystalline cellulose and 3.2 mg to 8 mg of colloidal silicon dioxide.

The capsule preparation of the present invention may optionally further contain an appropriate additional component commonly used for producing medical drugs, such as an excipient, a binder, a disintegrant, a lubricant, a diluent, a stabilizer, a tonicity agent, a pH regulator, a buffer, a dissolution aid, a suspension agent, a colorant, a preservative, an antiseptic agent or an antioxidant. DFP-11207 or a pharmaceutically acceptable salt thereof and a hygroscopic agent to be contained in the capsule preparation may be formed into, e.g., a powder or a granule, by themselves or together with other components (additives).

In the present invention, the coating for the capsule shell may comprise, or consist of, one or more bases commonly used in producing the coating. Examples of the base for the capsule coating include, but are not limited to, hydroxypropyl methylcellulose (HPMC), hydroxypropyl cellulose, methyl cellulose, carboxymethyl cellulose, agar, carrageenan, alginic acid, ghatti gum, gum Arabic, pullulan, Welan gum, xanthan gum, gellan gum, gum tragacanth, pectin, glucomannan, starch, polydextrose, dextrin, maltodextrin, cyclodextrin, indigestible dextrin, guar gum, tara gum, tamarind seed gum, locust bean gum, psyllium seed gum, Linseed gum, gelatin, casein, zein, sorbitol, maltitol, lactitol, Palatinit, xylitol, mannitol, galactitol and erythritol. In the present invention, the coating for the capsule shell preferably comprises or consists of HPMC.

The size of the capsule shell is not particularly limited as long as the size is good enough to house DFP-11207 or a pharmaceutically acceptable salt thereof, and a hygroscopic agent as mentioned above, and optionally an additional component, and suitable for oral administration. According to, e.g., the description of the Japanese Pharmacopoeia, the size of the capsule falls in the range of 000 (reference capacity: 1 g) to 5 (reference capacity: 0.03 g), preferably 00 (reference capacity: 0.5 g) to 4 (reference capacity: 0.06 g) such as 00 (reference capacity 0.5 g) to 3 (reference capacity 0.12 g), and more preferably 00 (reference capacity 0.5 g) to 2 (reference capacity: 0.2 g).

The capsule shell may have any one of forms: hard capsule shell, soft capsule shell and seamless capsule shell, and preferably hard capsule shell. The capsule shell may be colored or not, and transparent, translucent or opaque, and preferably, colored opaque capsule shell.

The capsule preparation of the present invention can be produced in accordance with a method for producing a capsule preparation commonly known in the technical field. More specifically, the capsule preparation can be produced by filling a capsule shell with DFP-11207 or a pharmaceutically acceptable salt thereof, and a hygroscopic agent as mentioned above, and optionally an additional component, for encapsulation.

The capsule preparation produced can be provided in a container together with a drying agent, and can be supplied, transported, sold and stored in the form.

In the present invention, the "container" may be any one of "hermetic container", "tight container" and "well-closed container" (defined by the Japanese Pharmacopoeia, 17th edition, general principle); and is preferably a moisture-proof container that can prevent moisture from entering. The container is preferable attached with a child-resistant cap.

The container may have any shape such as a bottle, a bag and a box, but the shape of the container is not limited to these. The container that can be used is formed of a highly moisture-proof material such as glass, a metal or a resin (e.g., polyethylene, polypropylene). The container is colored or not, and transparent, translucent or opaque, and preferably, a colored opaque container. The volume of the container, although it is not particularly limited, can be, for example, 50 to 500 mL (commonly, 50 mL, 100 mL, 150 mL, 180 mL, 200 mL, 250 mL, 300 mL, 350 mL, 400 mL, 450 mL or 500 mL), and preferably 100 to 200 mL.

In the present invention, examples of the "drying agent" include silica gel, alumina gel, zeolite, alumina, bauxite, anhydrous calcium sulfate, calcium chloride, lithium chloride, magnesium chloride, lime, clay, zeolite, talc, diatomaceous earth, white clay, carbon black, a high water-absorption resin, a synthetic resin powder, a sulfate, a carbonate, a hydroxide, an oxide, a chloride and a phosphate. The drying agents selected from these can be used singly or in combination. The form of the drying agent is not particularly limited. The drying agent can be packaged in a sachet, a pouch or a pack, and provided in a container together with a capsule preparation.

The amount of the drying agent to be contained in a container can be appropriately controlled in accordance with factors such as the amount and size of the capsule preparation, the size, shape and material of a container and the type of drying agent. For example, the drying agent of about 0.5 g to 10 g (e.g., 1 g to 8 g, 2 g to 5 g) per 100 mL of the volume of a container can be used. In an embodiment, 3 g of silica gel can be provided together with 50 capsules containing the preparation of the present invention in a white bottle (capacity 150 mL) made of high-density polyethylene.

The capsule preparation of the present invention has high stability compared to a single substance, DFP-11207 or a pharmaceutically acceptable salt thereof. In particular, the capsule preparation of the present invention can be more stable by providing it in a container together with a drying agent and can be stored at room temperature (25° C./humidity 50%) or in refrigerator (5° C.). The capsule preparation of the present invention can be highly stable for a long term (for example, 1 month or more, 2 month or more, 3 month or more, 4 month or more, 5 month or more, 6 month or more, 7 month or more, 8 month or more, or 9 month or more; and 84 month or less, 72 month or less, 60 month or less, 48 month or less, 36 month or less, 24 month or less, 18 month or less, or 12 month or less, although the upper limit is not particularly limited) particularly in low-temperature condition (e.g., 1 to 5° C.) within a refrigerator or the like. In the present invention, "be highly stable" means that denaturation or decomposition of a compound rarely or never occurs. This more specifically means that the purity measured by means of e.g., high performance liquid chromatography can be maintained at 90% or more, for example, 91% or more, 92% or more, 93% or more, 94% or more, 95% or more, 96% or more, 97% or more, 98% or more, or 99% or more.

The capsule preparation of the present invention is orally administered to cancer patients. The dosage amount may vary depending on factors such as the age, body weight and/or symptom of a patient, the type and/or severity of cancer and is an amount sufficient to treat cancer. The dosage amount of the capsule preparation of the present invention, more specifically, the amount of an active ingredient, DFP-11207 or a pharmaceutically acceptable salt thereof, is 50 mg to 500 mg, preferably 100 mg to 400 mg and more preferably 200 mg to 300 mg per day. The dosage amount selected from them can be administered once a day or is divided to two or more portions per day. The frequency of administration is once a day or 2 to 3 days, once a week, or once per 1 to 3 weeks.

In the present invention, the phrase "treat cancer" means reaching the state where cancer has completely disappeared. Other than this, the phrase means reaching the state where cancer temporarily or permanently shrinks or disappears and the state where cancer is in stable condition without worsening. For example, the phrase includes one or more phenomena such as reduction of cancer tumor-size, reduction of level of a tumor marker, symptomatic improvement of cancer, and extension of overall survival, progression-free survival or median survival used as a measure.

When DFP-11207 or a pharmaceutically acceptable salt thereof is orally administered, it is metabolized into EMFU slowly releasing 5-FU, CDHP serving as a 5-FU decomposition inhibitor, and CTA suppressing a toxicity to the lower gastrointestinal tract such as serious diarrhea, in the tissue of the lower gastrointestinal tract. After passing the lower gastrointestinal tract, EMFU slowly releases an anti-cancer active substance, 5-FU; and CDHP inhibits enzymatic decomposition of 5-FU with dihydropyrimidine dehydrogenase. In contrast, CTA stays in the tissue of the lower gastrointestinal tract and inhibits the activity of orotate phosphoribosyl transferase of the tissue. In this mechanism, 5-FU produces a maximum therapeutic effect while reducing 5-FU induced toxicity (e.g., serious diarrhea) to the lower gastrointestinal tract. For the reason, DFP-11207 or a pharmaceutically acceptable salt thereof can be extremely superior to existing 5-FU anti-cancer agents.

In the present invention, DFP-11207 is the same 5-FU series anti-cancer agent as 5-FU, TS-1 and Xeloda. Accordingly, examples of a target cancer for treatment include colorectal cancer, gastric cancer, esophageal cancer, pancreatic cancer, hepatocellular carcinoma, gallbladder cancer, gallbladder cancer, biliary tract cancer, breast cancer, ovarian cancer, breast cancer, cervical cancer, endometrial cancer, cervical cancer, and head and neck cancer. Since DFP-11207 has CDHP, which inhibits decomposition with dihydropyrimidine dehydrogenase (DPD) in a molecule, non-small cell lung cancer having a strong DPD activity can be included as a treatment target.

The capsule preparation of the present invention is characterized by having few side effects frequently associated with a 5-FU series anti-cancer agent, such as serious diarrhea, reduced white blood cell count, reduced neutrophil count and reduced platelet count.

The present invention will be more specifically described with reference to Examples but the technical scope of the present invention is not limited by these Examples.

EXAMPLES

Example 1

Capsule Preparation (100 mg) of DFP-11207 According to First Prescription

Table 1 shows the types/amounts of components of a capsule preparation (100 mg) of DFP-11207 according to the first prescription, and packages thereof.

The capsule preparation of DFP-11207 (100 mg) was prepared in accordance with the first prescription. White and opaque HMPC hard capsules of No. 2 in size were filled with DFP-11207 (100 mg), microcrystalline cellulose (56.8 mg) and colloidal silicon dioxide (3.2 mg) to prepare 50 capsule preparations. The capsule preparations were put in a 150-cc bottle made of high-density polyethylene (HDPE) with a 38-mm diameter mouth, and having 3 bags of silica gel (1 g per bag) for drying purpose placed therein. The bottle was closed with a child resistant cap.

TABLE 1

Types and amounts of components of capsule preparations of DFP-11207 (100 mg) according to the first prescription and packages thereof

| | | 100-mg Capsule of DFP-11207 | |
|---|---|---|---|
| Component | Manufacturer | mg/capsule | % w/w |
| DFP-11207 | — | 100.0 | 62.5 |
| Microcrystalline cellulose PH112, NF/EP/JP | FMC | 56.8 | 35.5 |
| Colloidal silicon dioxide, NF/EP/JP | Evonik | 3.2 | 2.0 |
| Filler content/capsule | | 160.0 | 100.0 |
| Capsule | Qualicaps | Size: No. 2 (white and opaque hard capsule made of HMPC) | |
| Bottle filled with capsules | Drug & Plastics Texas Technology | Child-resistant packaged 150-cc HDPE bottle with a 38 mm-diameter mouth Bag containing silica gel (1 g) for drying purpose | |
| Package | | Fifty capsules (100 mg)(silica gel (3 g) for drying purpose) per bottle | |

Table 2 shows long-term stability of a capsule preparation of DFP-11207 (100 mg) according to the first prescription at 5° C. and collection time (analysis time) of samples to be subjected to stability tests in acceleration conditions (25° C./humidity 60%) and severe conditions (30° C./humidity 65%).

TABLE 2

Analysis time of stability test samples of a capsule preparation of DFP-11207 (100 mg) according to the first prescription

| Conditions | \multicolumn{12}{c}{Analysis time (month)} | Number of test bottles | | |
|---|---|---|---|---|---|---|---|---|---|---|---|---|---|---|---|
| | 0 | 1 | 2 | 3 | 6 | 9 | 12 | 18 | 24 | 36 | 48 | 60ᶜ | Number of bottles tested | Number of bottles maintained | Total number of bottles |
| 5° C. | A | | | A | A | A | A | A | A | A | A | | 8 | 5 | 13 |
| 25° C./60% RH | | A | A | A | A | A | A | A | | | | | 8 | 4 | 12 |
| 30° C./65% RH | | A | A | A | A | A | | | | | | | 6 | 3 | 9 |
| Whole sum of test bottles | | | | | | | | | | | | | | | 34 |

Table 3 shows specifications of a capsule preparation of DFP-11207 (100 mg) according to the first prescription, stability test method (appearance (white, grayish white or cream) and purity (90% to 110%)) thereof and designation of test group. The purity was measured by high performance liquid chromatography (the same applies to the following tests).

TABLE 3

Specifications of a capsule preparation of DFP-11207 (100 mg) according to the first prescription, stability test method and designation of test group

| Characteristics | Method | Specifications | Number of test bottles Test group A |
|---|---|---|---|
| Appearance | ATM-1095 | White, grayish white, cream color capsule | 1 |
| Purity | ATM-1349 | 90.0-110.0% | |
| Analog | ATM-1349 | Individual related compounds: ≥0.1% (% area) Total: measured value | |
| Water content | USP <921> 1a | Measured value | |
| Disintegration time | USP <701> | Six individual disintegration times and their average | |
| Whole sum of test bottles | | | 1 |

Table 4-1 and Table 4-2 show data of a long-term stability test of a capsule preparation of DFP-11207 (100-mg) according to the first prescription, performed at 5° C.

Note that, hereinafter, "analog 1" is a compound represented by the following formula 2:

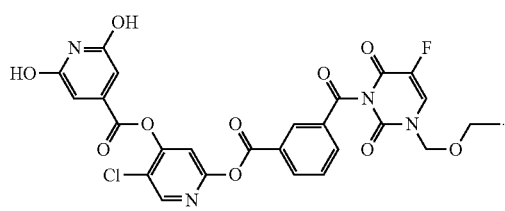

[Formula 2]

"Analog 2" is a compound represented by the following formula 3:

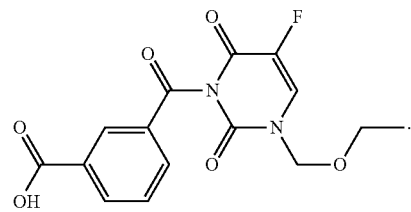

[Formula 3]

"Impurity 1" is a compound represented by the following formula 4:

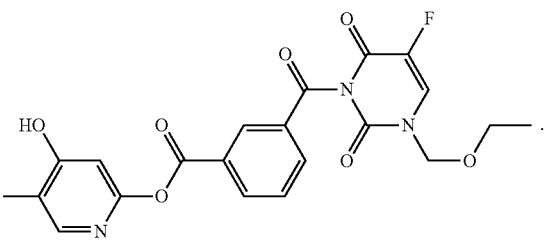

[Formula 4]

"Impurity 2" is a compound represented by the following formula 5:

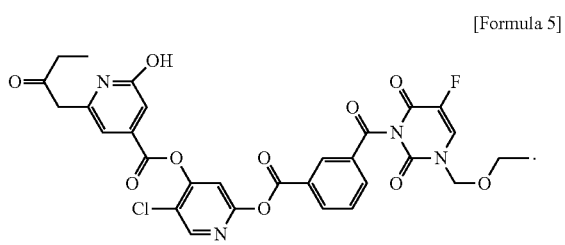 [SMILES: CCOCn1cc(F)c(=O)n(C(=O)c2cccc(C(=O)Oc3cc(OC(=O)c4cc(O)nc(CC(=O)CC)c4)c(Cl)cn3)c2)c1=O]

[Formula 5]

"Impurity 3" is a compound represented by the following formula 6:

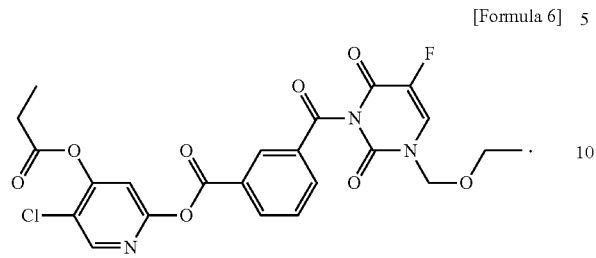

[Formula 6]

As shown in the results, the purity obtained after 48-month storage at 5° C. was 94.8% (within a reference range of 90.0 to 110.0). It was confirmed that the capsule preparation has stability for 48 months.

TABLE 4-1

Stability (at 5° C.) of capsule preparation of DFP-11207 (100 mg) according to the first prescription in real time

| Test | Method | Specifications | 0 month | 3 months<br>2016 Nov. 9 | 6 months<br>2017 Feb. 2 | 9 months<br>Analysis date<br>2017 May 10 | 12 months<br>2017 Aug. 10 | 18 months<br>2018 Aug. 12 |
|---|---|---|---|---|---|---|---|---|
| Appearance | ATM-1095 | White, grayish-white or cream color | Grayish-white | Grayish-white | Grayish-white | Grayish-white | Grayish-white | Grayish-white |
| Purity | ATM-1349 | 90.0-110.0% | 99.3% | 99.4% | 97.4% | 100.4% | 98.4% | 99.0% |
| Analog | ATM-1349 | Measured value ≥ 0.1% (Individual related compounds): % area Total: measured value | Analog 1: 0.1%<br>RRT 0.47: 0.1%<br>Impurity 1: 0.1%<br>RRT 0.61: 0.1%<br>Impurity 2: 0.4%<br>Impurity 3: 0.4%<br>RRT 0.88: 0.2%<br>RRT 0.90: 0.1%<br>RRT 0.92: 0.2%<br>RRT 0.94: 0.2%<br>RRT 1.03: 0.2%<br>Impurity 4: 0.3%<br>Total: 2.4% | Analog 2: 0.1%<br>Analog 11: 0.1%<br>RRT 0.46: 0.1%<br>Impurity 1: 0.2%<br>Impurity 2: 0.5%<br>RRT 0.79: 0.2%<br>Impurity 3: 0.5%<br>RRT 0.87: 0.2%<br>RRT 0.91: 0.1%<br>RRT 0.93: 0.1%<br>RRT 1.04: 0.1%<br>Impurity 4: 0.3%<br>Total: 2.5% | Analog 2: 0.1%<br>Analog 1: 0.1%<br>RRT 0.48: 0.1%<br>Impurity 1:0.1%<br>RRT 0.61: 0.1%<br>Impurity 2: 0.5%<br>RRT 0.80: 0.1%<br>Impurity 3: 0.4%<br>RRT 0.88: 0.2%<br>RRT 0.91: 0.1%<br>RRT 0.92: 0.1%<br>RRT 0.94: 0.1%<br>RRT 1.03: 0.2%<br>Impurity 4: 0.3%<br>Total: 2.5% | Analog 2: 0.1%<br>Analog 1: 0.1%<br>Impurity 1: 0.1%<br>Impurity 2: 0.5%<br>Impurity 3: 0.4%<br>RRT 0.87: 0.2%<br>RRT 0.88: 0.1%<br>RRT 0.91: 0.1%<br>RRT 0.93: 0.1%<br>RRT 1.03: 0.1%<br>Impurity 4: 0.3%<br>Total: 2.2% | Analog 2: 0.1%<br>Analog 1: 0.1%<br>RRT 0.46: 0.1%<br>Impurity 1: 0.1%<br>RRT 0.60: 0.1%<br>Impurity 2: 0.5%<br>RRT 0.79: 0.1%<br>Impurity 3: 0.5%<br>RRT 0.87: 0.2%<br>RRT 0.90: 0.1%<br>RRT 0.91: 0.1%<br>RRT 1.04: 0.1%<br>Impurity 4: 0.3%<br>Total: 2.5% | Analog 2: 0.1%<br>Analog 1: 0.1%<br>RRT 0.46: 0.1%<br>Impurity 1: 0.2%<br>Impurity 2: 0.5%<br>RRT 0.79: 0.1%<br>Impurity 3: 0.4%<br>RRT 0.87: 0.2%<br>RRT 0.90: 0.1%<br>RRT 0.91: 0.1%<br>RRT 0.93: 0.2%<br>RRT 1.04: 0.2%<br>Impurity 4: 0.3%<br>Total: 2.6% |
| Water content | USP <921> Ia | Measured value | 1.6% | 1.1% | 1.2% | 1.3% | 1.5% | 1.2% |
| Disintegration time | USP <701> | Measured value | 1:59, 1:51, 1:38<br>1:51, 1:59, 2:14<br>Average value: 1:55 | 1:34, 1:31, 1:34<br>1:32, 1:28, 1:37<br>Average value: 1:33 | 1:37, 2:15, 2:23<br>2:26, 2:26, 2:41<br>Average value: 2:18 | 1:25, 1:30, 1:32,<br>1:33, 1:35, 1:40<br>Average value: 1:33 | 1:40, 1:50, 1:57,<br>2:04, 2:08, 2:2<br>Average value: 2:00 | 1:30, 1:33, 1:40,<br>1:42, 1:45, 1:50<br>Average value: 1:40 |

Note)
Relative Retention Time (Relative elution time) of RRT:HPLC (High performance liquid chromatography)

TABLE 4-2

Stability (at 5° C.) of capsule preparation of DFP-11207 (100 mg) according to the first prescription in real time

| Test item | Method | Specifications | 24 months 2018 Aug. 10 | 36 months Analysis date 2019 Aug. 12 | 48 months 2020 Aug. 10 | 60 month |
|---|---|---|---|---|---|---|
| Appearance | ATM-1095 | | Grayish-white | Grayish-white | Grayish-white | |
| Purity | ATM-1349 | 90.0-110.0% | 102.9% | 100.5% | 94.8% | |
| Analog | ATM-1349 | Measured value ≥ 0.1% (Individual related compounds): % area Total: measured value | Analog 2: 0.1%<br>Analog 1: 0.1%<br>RRT 0.46: 0.1%<br>Impurity 1: 0.2%<br>RRT 0.61: 0.1%<br>Impurity 2: 0.6%<br>RRT 0.79: 0.1%<br>Impurity 3: 0.4%<br>RRT 0.87: 0.2%<br>RRT 0.89: 0.1%<br>RRT 0.90: 0.2%<br>RRT 0.91: 0.2%<br>RRT 0.93: 0.2%<br>RRT 1.04: 0.2%<br>Impurity 4: 0.3%<br>Total: 3.1% | Analog 2: 0.1%<br>Analog 1: 0.1%<br>RRT 0.46: 0.1%<br>Impurity 1: 0.2%<br>RRT 0.61: 0.1%<br>Impurity 2: 0.6%<br>RRT 0.79: 0.2%<br>Impurity 3: 0.5%<br>RRT 0.87: 0.2%<br>RRT 0.90: 0.1%<br>RRT 0.91: 0.1%<br>RRT 0.93: 0.1%<br>RRT 1.04: 0.1%<br>RRT 1.06: 0.1%<br>Impurity 4: 0.3%<br>RRT 1.24: 0.1%<br>Total: 3.0% | Analog 2: 0.2%<br>Analog 1: 0.2%<br>RRT 0.46: 0.1%<br>Impurity 1: 0.4%<br>RRT 0.61: 0.1%<br>Impurity 2: 1.5%<br>RRT 0.79: 0.2%<br>Impurity 3: 0.4%<br>RRT 0.87: 0.3%<br>RRT 0.88: 0.1%<br>RRT 0.90: 0.1%<br>RRT 0.91: 0.1%<br>RRT 0.93: 0.1%<br>RRT 1.04: 0.1%<br>RRT 1.06: 0.1%<br>Impurity 4: 0.3%<br>RRT 1.24: 0.1%<br>Total: 4.4% | |
| Water content | USP <921> Ia | Measured value | 1.5% | 1.7% | 2.0% | |
| Disintegration time | USP <701> | Measured value | 1:15, 1:18, 1:20, 1:30, 1:40, 1:45<br>Average value: 1:28 | 1:40, 1:20, 1:24, 1:27, 1:30, 1:15<br>Average value: 1:26 | 1:29, 1:31, 1:40, 1:46, 1:47, 1:56<br>Average value: 1:42 | |

Table 5 shows stability test data of capsule preparation of DFP-11207 (100 mg) according to the first prescription in acceleration conditions (25° C./humidity 60%).

As shown in the results, it was confirmed that the capsule preparation is stable for 6 months. The purities in the 9th month and 12th month were both lower than the specified value (90% to 110%). Stability was not confirmed.

TABLE 5

Stability of capsule preparation of DFP-11207 (100 mg) according to the first prescription in acceleration conditions (25° C./60 RH)

| Test | Method | Specifications | 0 month 2016 Sep. 12 | 1 month 2016 Oct. 10 | 2 months 2016 Nov. 19 | 3 months 2017 Feb. 8 | 6 months Analysis date 2017 May 10 | 9 months 2017 Aug. 10 | 12 months | 18 months | 24 months |
|---|---|---|---|---|---|---|---|---|---|---|---|
| Appearance | ATM-1095 | White, grayish-white or cream color | Grayish-white | Grayish-white | Grayish-white | Grayish-white | Grayish-white | Grayish-white | Cream color | | |
| Purity | ATM-1349 | 90.0-110.0% | 99.3% | 98.6% | 98.5% | 93.7%** | 97.4% | 85.8%, 89.7%. 83.5%, 88.9% | 76.9% | | |
| Analog | ATM-1349 | Measured value ≥ 0.1% (Individual related com- | Analog 1: 0.1%<br>RRT 0.47: 0.1%<br>Impurity 1: 0.1%<br>RRT 0.61: 0.1% | Analog 2: 0.2%<br>RRT 0.37: 0.1%<br>Analog 1: 0.1%<br>RRT 0.45: 0.1% | Analog 2: 0.2%<br>Analog 1: 0.1%<br>RRT 0.45: 0.1%<br>Impurity 1: 0.3% | Analog 2: 0.3%<br>Analog 1: 0.2%<br>RRT 0.46: 0.1%<br>Impurity 1: 0.3% | Analog 2: 0.4%<br>RRT 0.37: 0.1%<br>RRT 0.48: 0.1% | Analog 2: 1.9%<br>RRT 0.31: 0.3%<br>RRT 0.33: 0.1%<br>RRT 0.36: 0.2% | Analog 2: 4.5%<br>RRT 0.31: 1.0%<br>RRT 0.33: 0.2%<br>RRT 0.36: 0.3% | | |

TABLE 5-continued

Stability of capsule preparation of DFP-11207 (100 mg) according to the first prescription in acceleration conditions (25° C./60 RH)

| Test | Method | | 0 month | 1 month | 2 months | 3 months | 6 months | 9 months | 12 months | 18 months | 24 months |
|---|---|---|---|---|---|---|---|---|---|---|---|
| | | | \multicolumn{7}{c}{Analysis date} | | |
| | | | 2016 Sep. 12 | 2016 Oct. 10 | 2016 Nov. 19 | 2017 Feb. 8 | 2017 May 10 | 2017 Aug. 10 | | | |
| | | pounds): % area Total: measured value | Impurity 2: 0.4% Impurity 3: 0.4% RRT 0.88: 0.2% RRT 0.90: 0.1% RRT 0.92: 0.2% RRT 0.94: 0.2% RRT 1.03: 0.2% Impurity 4: 0.3% Total: 2.4% | Impurity 1: 0.2% RRT 0.59: 0.1% Impurity 2: 0.6% RRT 0.79: 0.1% Impurity 3: 0.4% RRT 0.87: 0.3% RRT 0.89: 0.1% RRT 0.91: 0.2% RRT 0.93: 0.2% RRT 1.04: 0.2% RRT 1.06: 0.1% Impurity 4: 0.3% Total: 3.3% | RRT 0.59: 0.1% Impurity 2: 0.8% RRT 0.79: 0.1% Impurity 3: 0.4% RRT 0.87: 0.2% RRT 0.89: 0.1% RRT 0.91: 0.1% RRT 0.93: 0.1% RRT 1.04: 0.2% Impurity 4: 0.3% Total: 3.2% | Impurity 2: 1.1% RRT 0.79: 0.1% Impurity 3: 0.4% RRT 0.87: 0.2% RRT 0.91: 0.1% RRT 0.93: 0.1% RRT 1.04: 0.2% Impurity 4: 0.3% Total: 3.4% | Impurity 1: 0.5% RRT 0.61: 0.1% Impurity 2: 1.8% RRT 0.80: 0.3% Imp-3: 0.4% RRT 0.88: 0.2% RRT 0.91: 0.1% RRT 0.92: 0.1% RRT 0.94: 0.2% RRT 1.03: 0.2% Impurity 4: 0.3% Total: 5.2% | Analog 1: 1.0% Impurity 1: 1.4% RRT 0.55: 0.1% Impurity 2: 4.0% RRT 0.79: 0.5% Impurity 3: 0.7% RRT 0.83: 0.3% RRT 0.87: 0.2% RRT 0.88: 0.1% RRT 0.91: 0.1% RRT 0.93: 0.2% RRT 1.03: 0.3% Impurity 4: 0.4% Total: 11.8% | Analog 1: 1.8% Impurity 1: 1.5% RRT 0.49: 0.1% RRT 0.55: 0.4% RRT 0.60: 0.1% RRT 0.67: 0.1% Impurity 2: 6.0% RRT 0.79: 0.6% Impurity 3: 0.6% RRT 0.84: 0.9% RRT 0.87: 0.2% RRT 0.89: 0.2% RRT 0.90: 0.1% RRT 0.91: 0.1% RRT 0.93: 0.3% RRT 1.04: 0.6% Impurity 4: 0.2% Total: 19.8% | | |
| Water content | USP <921> Ia | Measured value | 1.6% | 1.3% | 1.5% | 1.3% | 1.1% | 1.3% | 1.5% | | |
| Disintegration time | USP <701> | Measured value | 1:59, 1:51, 1:38 1:51, 1:59, 2:14 Average value: 1:55 | 1:40, 1:40, 1:46 1:52, 1:57, 1:58 Average value: 1:49 | 1:23, 1:43, 1:29 1:35, 1:38, 1.45 Average value: 1:36 | 1:25, 1:29, 1:36 1:22, 1:27, 1:30 Average value: 1:29 | 1:43, 2:19, 2:20 2:22, 2:23, 2:24 Average value: 2:15 | 1:21, 1:32, 1:36 1:43, 1:49, 1:55 Average value: 1:39 | 1:59, 2:06, 2:15, 2:18, 2:30, 2:42 Average value: 2:18 | | |

Table 6 shows the stability test data of a capsule preparation of DFP-11207 (100 mg) according to the first prescription in severe conditions (30° C./humidity 65%).

As shown in the results, it was confirmed that the capsule preparation is stable for 3 months and not stable on and after 3 months. The appearance of the capsule preparation changed from grayish-white to slightly brown.

TABLE 6

Stability of capsule preparation of DFP-11207 (100 mg) according to the first prescription in severe conditions (30° C./65 RH)

| Test | Method | Specifications | 0 month | 1 month | 2 months | 3 months | 6 months | 9 months | 12 months |
|---|---|---|---|---|---|---|---|---|---|
| | | | | Analysis date | | | | | |
| | | | | 2016 Sep. 12 | 2016 Oct. 10 | 2016 Nov. 9 | 2017 Feb. 8 | | |
| Appearance | ATM-1095 | White, grayish-white or cream color | Grayish-white | Grayish-white | Grayish-white | Grayish-white | Slightly brown | | |
| Purity | ATM-1349 | 90.0-110.0% | 99.3% | 95.8% | 95.3% | 92.7% | | | |
| Analog | ATM-1349 | Individual related compounds: Measured value ≥ 0.1% (% area) Total: measured value | Analog 1: 0.1% RRT 0.47: 0.1% Impurity 1: 0.1% RRT 0.61: 0.1% Impurity 2: 0.4% Impurity 3: 0.4% RRT 0.88: 0.2% RRT 0.90: 0.1% RRT 0.92: 0.2% RRT 0.94: 0.2% RRT 1.03: 0.2% Impurity 4: 0.3% Total: 2.4% | Analog 2: 0.3% Analog 1: 0.2% RRT 0.45: 0.1% Impurity 1: 0.3% RRT 0.59: 0.1% Impurity 2: 0.8% RRT 0.79: 0.1% Impurity 3: 0.4% RRT 0.87: 0.2% RRT 0.89: 0.1% RRT 0.91: 0.2% RRT 0.93: 0.2% RRT 1.04: 0.2% RRT 1.06: 0.1% Impurity 4: 0.3% Total: 3.6% | Analog 2: 0.4% Analog 1: 0.3% RRT 0.45: 0.1% Impurity 1: 0.5% RRT 0.59: 0.1% Impurity 2: 1.6% RRT 0.79: 0.2% Impurity 3: 0.4% RRT 0.87: 0.2% RRT 0.89: 0.1% RRT 0.91: 0.1% RRT 0.93: 0.1% RRT 1.04: 0.2% Impurity 4: 0.3% Total: 4.6% | Analog 2: 0.7% RRT 0.36: 0.1% Analog 1: 0.5% Impurity 1: 1.0% Impurity 2: 2.3% RRT 0.79: 0.2% Impurity 3: 0.5% RRT 0.84: 0.1% RRT 0.87: 0.2% RRT 0.91: 0.1% RRT 0.93: 0.2% RRT 1.04: 0.3% Impurity 4: 0.3% Total: 6.5% | | | |
| Water content | USP <921> Ia | Measured value | 1.6% | 1.2% | 1.5% | 1.1% | | | |
| Disintegration time | USP <701> | Measured value | 1:59, 1:51, 1:38 1:51, 1:59, 2:14 Average value: 1:55 | 2:02, 2:10, 2:16 2:16, 2:30, 2:31 Average value: 2:18 | 1:43, 1:31, 1:39, 1:35, 1:44, 1:22 Average value: 1:36 | 1:40, 1:37, 1:32, 1:18, 1:26, 1:28 Average value: 1:30 | | | |

Example 2

Capsule Preparation (100 mg) of DFP-11207 According to the Second Prescription

Table 7 shows the types/amounts of components of a capsule preparation (100 mg) of DFP-11207 according to the second prescription, and packages thereof.

The capsule preparation of DFP-11207 (100 mg) was prepared in accordance with the second prescription. White and opaque hard HMPC capsules of No. 00 in size were filled with DFP-11207 (100 mg), microcrystalline cellulose (292.0 mg) and colloidal silicon dioxide (8.0 mg) to prepare 50 capsule preparations. The capsule preparations were put in a 150-cc bottle made of high density polyethylene (HDPE) with a 38-mm diameter mouth and having 3 bags of silica gel (1 g per bag) for drying purpose placed therein. The bottle was closed with a child resistant cap.

TABLE 7

Types and amounts of components of capsule preparation of DFP-11207 (100 mg) according to the second prescription and packages thereof

| | | 100-mg Capsule of DFP-11207 | |
|---|---|---|---|
| Component | Manufacturer | mg/capsule | % w/w |
| DFP-11207 | — | 100.0 | 25.0 |
| Microcrystalline cellulose PH112, NF/EP/JP | FMC | 292.0 | 73.0 |
| Colloidal silicon dioxide, NF/EP/JP | Evonik | 8.000 | 2.0 |
| Filler content/capsule | | 400.0 | 100.0 |
| Capsule | Qualicaps | Size No. 00 (white and opaque hard capsule made of HMPC) | |
| Bottle filled with capsules | Drug & Plastics | Child-resistant packaged 150-cc HDPE bottle with a 38 mm-diameter mouth | |
| Package | Texas Technology | Bag containing silica gel (1 g) for drying purpose Fifty capsules (100 mg) (silica gel (3 g) for drying purpose) per bottle | |

Table 8 shows long-term stability of a capsule preparation of DFP-11207 (100 mg) according to the second prescription at 5° C. and collection time (analysis time) of samples to be subjected to stability tests in acceleration conditions (25° C./humidity 60%) and severe conditions (30° C./humidity 65%).

TABLE 8

Analysis time of stability test samples of a capsule preparation of DFP-11207 (100 mg) according to the second prescription

| Conditions | \multicolumn{13}{c|}{Analysis time (month)} | Number of bottles tested | Number of bottles maintained | Total number of bottles |
|---|---|---|---|---|---|---|---|---|---|---|---|---|---|---|---|---|
|  | 0 | 1 | 2 | 3 | 6 | 9 | 12 | 18 | 24 | 36 | 48 | 60 | 72 | 84 |  |  |  |
| 5° C. | A |  |  | B | A | B | A | A | A | A | A | A | A | A | 20 | 10 [c] | 30 |
| 25° C./60% RH |  | B | B | B | A | B | A | A | A |  |  |  |  |  | 12 | 6 | 18 |
| 30° C./65% RH |  | B | B | B | A | B | A |  |  |  |  |  |  |  | 8 | 4 | 12 |
| Whole sum of test bottles |  |  |  |  |  |  |  |  |  |  |  |  |  |  |  |  | 60 |

Table 9 shows specifications of a capsule preparation of DFP-11207 (100 mg) according to the second prescription, stability test method and designation of test groups.

TABLE 9

Specifications of a capsule preparation of DFP-11207 (100 mg) according to the second prescription, stability test method and designation of test groups

| Characteristics | Method | Specifications | Number of test bottles | |
|---|---|---|---|---|
|  |  |  | Test group A | Test group B |
| Appearance | ATM-1095 | White, grayish white, cream color capsule | 1 | 1 |
| Purity | ATM-1349 | 90.0 - 110.0% |  |  |
| Analog | ATM-1349 | Individual related compounds: ≥0.1% (% area) Total: measured value |  |  |
| Water content | USP <921> 1a | Measured value |  |  |
| Disintegration time | USP <701> | Six individual disintegration times and their average |  |  |
| Microbial content | USP <61> USP <62> | Total Aerobic Microbial Count (TAMC) ≤$10^3$ cfu/g Total Combined Yeasts and Molds Count (TYMC) ≤$10^2$ cfu/g Escherichia coli: Absent | 1 |  |
| Whole sum of test bottles |  |  | 2 | 1 |

Table 10 shows data obtained in the middle of a long-term stability test (stability test in real time) of a capsule preparation of DFP-11207 (100 mg) according to the second prescription, performed at 5° C.

As shown in the results, the purity obtained after storage for 9 months at 5° C. was 103.7% (within a reference range of 90.0 to 110.0). It was estimated that a capsule preparation has long-term stability at 5° C.

TABLE 10

Stability (at 5° C.) of capsule preparation of DFP-11207 (100 mg) according to the second prescription in real time

| Test | Method | Specifications | 0 month | 3 months | 6 months | 9 months | 12 months | 18 months |
|---|---|---|---|---|---|---|---|---|
|  |  |  |  | \multicolumn{3}{c|}{Analysis date} |  |  |
|  |  |  |  | 2020 Jul. 1 | 2020 Oct. 2 | 2021 Jan. 4 |  |  |
| Appearance | ATM-1095 | White, grayish-white or cream color | Grayish-white | Grayish-white | Grayish-white | Grayish-white |  |  |
| Purity | ATM-1349 | 90.0-110.0% | 100.3% | 103.3% | 101.9% | 103.7% |  |  |
| Analog | ATM-1349 | Individual related compounds: Measured value ≥ 0.1% (% area) Total: measured value | Impurity 1: 0.1% Impurity 2: 0.3% Impurity 3: 0.5% RRT 0.87: 0.1% RRT 0.90: 0.1% RRT 0.91: 0.2% RRT 0.93: 0.2% RRT 1.04: 0.1% Impurity 4: 0.4% RRT 1.31: 0.1% | Analog 2: 0.1% Impurity 1: 0.1% Impurity 2: 0.3% Impurity 3: 0.5% RRT 0.87: 0.1% RRT 0.88: 0.1% RRT 0.90: 0.2% RRT 0.91: 0.2% RRT 0.93: 0.1% RRT 1.04: 0.1% | Analog 2: 0.1% Impurity 1: 0.1% Impurity 2: 0.4% Impurity 3: 0.5% RRT 0.87: 0.1% RRT 0.90: 0.1% RRT 0.91: 0.1% RRT 1.04: 0.1% Impurity 4: 0.4% RRT 1.31: 0.1% | Analog 2: 0.1% Impurity 1: 0.4% Impurity 2: 0.3% RRT 0.81: 0.1% Impurity 3: 0.5% RRT 0.87: 0.1% RRT 0.90: 0.1% RRT 0.91: 0.1% RRT 0.93: 0.1% RRT 1.04: 0.2% |  |  |

TABLE 10-continued

Stability (at 5° C.) of capsule preparation of DFP-11207 (100 mg) according to the second prescription in real time

| | | | Specifications | | | | | |
|---|---|---|---|---|---|---|---|---|
| | | | 0 month | 3 months | 6 months | 9 months | 12 months | 18 months |
| | | | | | Analysis date | | | |
| Test | Method | | | 2020 Jul. 1 | 2020 Oct. 2 | 2021 Jan. 4 | | |
| | | | RRT 1.32: 0.1% RRT 1.53: 0.1% Total: 2.3% | Impurity 4: 0.4% RRT 1.31: 0.1% RRT 1.32: 0.1% Total: 2.4% | RRT 1.32: 0.1% Total: 2.1% | Impurity 4: 0.4% Total: 2.4% | | |
| Water content | USP <921> Ia | Measured value | 1.4% | 2.0% | 1.7% | 1.7% | | |
| Disinte-gration time | USP <701> | Average of measured values | 1:56, 2:18, 1:58, 1:46, 1:54, 2:29 Average value: 2:04 | 1:33, 1:42, 1:45, 2:00, 2:10, 2:18 Average value: 1:55 | 1:14, 1:35, 1:38, 1:45, 1:53, 2:03 Average value: 1:41 | 1:23, 1:31, 1:37, 1:46, 1:52, 2:16 Average value: 1:44 | | |
| Micro-bial content | USP <61> USP <62> | | Total Aerobic Microbial Count (TAMC) ≤ $10^3$ cfu/g Total Combined Yeasts and Molds Count (TYMC) ≤ $10^2$ cfu/g *Escherichia coli*: Absent | Total Aerobic Microbial Count (TAMC) ≤ 10 cfu/g Total Combined Yeasts and Molds Count (TYMC) ≤ 10 cfu/g *Escherichia coli*: Absent | | Total Aerobic Microbial Count (TAMC) ≤ 10 cfu/g Total Combined Yeasts and Molds Count (TYMC) ≤ 10 cfu/g *Escherichia coli*: Absent | | |

Table 11-1 and Table 11-2 show data obtained in the middle of the stability test of a capsule preparation of DFP-11207 (100 mg) according to the second prescription in acceleration conditions (25° C./humidity 60%).

As shown in the results, it was estimated that the capsule preparation has long term stability for 9 months or more. Significant improvement was confirmed compared to the stable period (6 months) of the capsule preparation of DFP-11207 (100 mg) according to the first prescription in acceleration conditions (25° C./humidity 60%).

TABLE 11-1

Stability of capsule preparation of DFP-11207 (100 mg) according to the second prescription in acceleration conditions (25° C./60 RH)

| | | | Specifications | | | | |
|---|---|---|---|---|---|---|---|
| | | | 0 month | 1 month | 2 months | 3 months | 6 months |
| | | | | | Analysis date | | |
| Test | Method | | | 2020 May 1 | 2020 Jun. 1 | 2020 Jun. 1 | 2020 Oct. 2 |
| Appear-ance | ATM-1095 | White, grayish-white or cream color | Grayish-white | Grayish-white | Grayish-white | Grayish-white | Grayish-white |
| Purity | ATM-1349 | 90.0-110.0% | 100.3% | 100.6% | 102.8% | 103.7% | 104.5% |
| Analog | ATM-1349 | Individual related compounds: Measured value ≥ 0.1% (% area) Total: measured value | Impurity 1: 0.1% Impurity 2: 0.3% Impurity 3: 0.5% RRT 0.87: 0.1% RRT 0.90: 0.1% RRT 0.91: 0.2% RRT 0.93: 0.2% RRT 1.04: 0.1% Impurity 4: 0.4% RRT 1.31: 0.1% RRT 1.32: 0.1% RRT 1.53: 0.1% | Analog 2: 0.1% RRT 0.50: 0.1% Impurity 1: 0.1% Impurity 2: 0.4% RRT 0.81: 0.1% RRT 0.87: 0.1% RRT 0.90: 0.1% RRT 0.91: 0.2% RRT 0.93: 0.1% RRT 0.94: 0.1% RRT 1.04: 0.1% | Analog 2: 0.1% Impurity 1: 0.1% Impurity 2: 0.5% RRT 0.81: 0.1% RRT 0.87: 0.5% Impurity 3: 0.5% RRT 0.88: 0.1% RRT 0.90: 0.2% RRT 0.91: 0.2% RRT 0.93: 0.1% RRT 1.04: 0.1% Impurity 4: 0.4% | Analog 2: 0.1% Impurity 1: 0.3% Impurity 2: 0.4% Impurity 3: 0.5% RRT 0.87: 0.1% RRT 0.88: 0.1% RRT 0.90: 0.2% RRT 0.91: 0.2% RRT 0.93: 0.1% RRT 1.04: 0.1% Impurity 4: 0.5% RRT 1.31: 0.1% | Analog 2: 0.1% Analog 1: 0.1% Impurity 1: 0.1% Impurity 2: 0.9% RRT 0.81: 0.1% RRT 0.87: 0.1% Impurity 3: 0.5% RRT 0.87: 0.1% RRT 0.90: 0.1% RRT 0.91: 0.1% RRT 0.93: 0.1% RRT 1.04: 0.2% Impurity 4: 0.4% |

TABLE 11-1-continued

Stability of capsule preparation of DFP-11207 (100 mg) according to the second prescription in acceleration conditions (25° C./60 RH)

| | | | Specifications | | | | |
|---|---|---|---|---|---|---|---|
| | | | 0 month | 1 month | 2 months | 3 months | 6 months |
| | | | | | Analysis date | | |
| Test | Method | | | 2020 May 1 | 2020 Jun. 1 | 2020 Jun. 1 | 2020 Oct. 2 |
| | | | Total: 2.3% | Impurity 4: 0.4%<br>RRT 1.31: 0.1%<br>RRT 1.32: 0.1%<br>RRT 1.41: 0.1%<br>Total: 2.7% | RRT 1.31: 0.1%<br>RRT 1.32: 0.1%<br>Total: 2.7% | RRT 1.32: 0.1%<br>Total: 2.8% | RRT 1.24: 0.1%<br>RRT 1.31: 0.1%<br>RRT 1.32: 0.1%<br>Total: 3.1% |
| Water content | USP <921> Ia | Measured value | 1.4% | 1.6% | 2.4% | 1.7% | 2.4% |
| Disintegration time | USP <701> | Average of measured values | 1:56, 2:18, 1:58, 1:46, 1:54, 2:29<br>Average value: 2:04 | 1:58, 1:41, 1:45, 1:50, 2:00, 2:25<br>Average value: 1:57 | 2:08, 1:38, 1:48, 2:15, 1:30, 2:01<br>Average value: 1:53 | 1:07, 1:14, 1:26, 1:40, 1:48, 2:02<br>Average value: 1:33 | 1:08, 1:20, 1:31, 1:44, 1:51, 1:59<br>Average value: 1:36 |
| Microbial content | USP <61><br>USP <62> | | Total Aerobic Microbial Count (TAMC) ≤ $10^3$ cfu/g Total Combined Yeasts and Molds Count (TYMC) ≤ $10^2$ cfu/g<br>*Escherichia coli*: Absent | Total Aerobic Microbial Count (TAMC) ≤ 10 cfu/g Total Combined Yeasts and Molds Count (TYMC) ≤ 10 cfu/g<br>*Escherichia coli*: Absent | | | Total Aerobic Microbial Count (TAMC) ≤ 10 cfu/g Total Combined Yeasts and Molds Count (TYMC) ≤ 10 cfu/g<br>*Escherichia coli*: Absent |

TABLE 11-2

Stability of capsule preparation of DFP-11207 (100 mg) according to the second prescription in acceleration conditions (25° C./60 RH)

| | | | Specifications | | | | |
|---|---|---|---|---|---|---|---|
| | | | 8 months | 9 months | 12 months | 18 months | 24 months |
| | | | | Analysis date | | | |
| Test | Method | | 2020 Dec. 4 | 2021 Jan. 4 | | | |
| Appearance | ATM-1095 | White, grayish-white or cream color | Grayish-white | Grayish-white | | | |
| Purity | ATM-1349 | 90.0-110.0% | 101.9% | 104.3% | | | |
| Analog | ATM-1349 | Individual related compounds: Measured value ≥ 0.1% (% area) Total: measured value | Analog 2: 0.1%<br>Analog 1: 0.1%<br>Impurity 1: 0.4%<br>Impurity 2: 0.9%<br>RRT 0.81: 0.2%<br>Impurity 3: 1.0%<br>RRT 0.87: 0.1%<br>RRT 0.90: 0.1%<br>RRT 0.91: 0.1%<br>RRT 0.94: 0.1%<br>RRT 1.04: 0.2%<br>Impurity 4: 0.4%<br>RRT 1.32: 0.2%<br>Total: 3.9% | Analog 2: 0.2%<br>Analog 1: 0.1%<br>Impurity 1: 0.6%<br>Impurity 2: 1.0%<br>RRT 0.81: 0.2%<br>Impurity 3: 0.5%<br>RRT 0.87: 0.1%<br>RRT 0.90: 0.1%<br>RRT 0.91: 0.1%<br>RRT 0.93: 0.1%<br>RRT 1.04: 0.2%<br>Impurity 4: 0.4%<br>Total: 3.6% | | | |
| Water content | USP <921> Ia | Measured value | 1.5% | 1.7% | | | |
| Disintegration time | USP <701> | Average of measured values | 1:50, 1:46, 1:52, 1:58, 2:10, 2:15<br>Average value: 1:59 | 1:19, 1:29, 1:41, 1:50, 1:59, 2:19<br>Average value: 1:46 | | | |

TABLE 11-2-continued

Stability of capsule preparation of DFP-11207 (100 mg) according to the second prescription in acceleration conditions (25° C./60 RH)

| | | | Specifications | | | | | |
|---|---|---|---|---|---|---|---|---|
| | | | 8 months | 9 months | 12 months | 18 months | 24 months | |
| | | | Analysis date | | | | | |
| Test | Method | | 2020 Dec. 4 | 2021 Jan. 4 | | | | |
| Microbial content | USP <61> USP <62> | Total Aerobic Microbial Count (TAMC) ≤ $10^3$ cfu/g Total Combined Yeasts and Molds Count (TYMC) ≤ $10^2$ cfu/g *Escherichia coli*: Absent | | | | | | |

Table 12-1 and Table 12-2 further show data obtained in the middle of the stability test of a capsule preparation of DFP-11207 (100 mg) according to the second prescription in severe conditions (30° C./humidity 65%).

As shown in the results, it was estimated that the capsule preparation is stable for at least 9-months. Significant improvement was confirmed compared to the stable period (3 months) of the capsule preparation of DFP-11207 (100 mg) according to the first prescription in the severe conditions (30° C./humidity 65%).

TABLE 12-1

Stability of capsule preparation of DFP-11207 (100 mg) according to the second prescription in severe conditions (30° C./65% RH)

| | | | Specifications | | | | |
|---|---|---|---|---|---|---|---|
| | | | 0 month | 1 month | 2 months | 3 months | 6 months |
| | | | | | Analysis date | | |
| Test | Method | | | 2020 May 1 | 2020 Jun. 1 | 2020 Jun. 1 | 2020 Oct. 2 |
| Appearance | ATM-1095 | White, grayish-white or cream color | Grayish-white | Grayish-white | Grayish-white | Grayish-white | Grayish-white |
| Purity | ATM-1349 | 90.0-110.0% | 100.3% | 101.7% | 102.2% | 104.1% | 99.8% |
| Analog | ATM-1349 | Individual related compounds: Measured value ≥ 0.1% (% area) Total: measured value | Impurity 1: 0.1% Impurity 2: 0.3% Impurity 3: 0.5% RRT 0.87: 0.1% RRT 0.90: 0.1% RRT 0.91: 0.2% RRT 0.93: 0.2% RRT 1.04: 0.1% Impurity 4: 0.4% RRT 1.31: 0.1% RRT 1.32: 0.1% RRT 1.53: 0.1% Total: 2.3% | Analog 2: 0.1% RRT 0.50: 0.1% Impurity 1: 0.2% Impurity 2: 0.5% RRT 0.81: 0.1% Impurity 3: 0.5% RRT 0.87: 0.1% RRT 0.90: 0.1% RRT 0.91: 0.2% RRT 0.93: 0.1% RRT 0.94: 0.1% RRT 1.04: 0.1% Impurity 4: 0.4% RRT 1.31: 0.1% RRT 1.32: 0.1% RRT 1.48: 0.1% Total: 2.9% | Analog 2: 0.2% Analog 1: 0.1% Impurity 2: 0.7% RRT 0.81: 0.2% Impurity 3: 0.5% RRT 0.87: 0.1% RRT 0.88: 0.1% RRT 0.90: 0.2% RRT 0.91: 0.2% RRT 0.93: 0.1% RRT 1.04: 0.1% Impurity 4: 0.4% RRT 1.31: 0.1% RRT 1.32: 0.1% Total: 3.2% | Analog 2: 0.1% Analog 1: 0.1% Impurity 2: 0.8% RRT 0.81: 0.1% Impurity 3: 0.5% RRT 0.87: 0.1% RRT 0.88: 0.1% RRT 0.90: 0.2% RRT 0.91: 0.2% RRT 0.93: 0.1% RRT 1.04: 0.1% Impurity 4: 0.4% RRT 1.31: 0.1% RRT 1.32: 0.1% Total: 3.2% | Analog 2: 0.3% Analog 1: 0.2% Impurity 1: 0.4% Impurity 2: 1.8% RRT 0.81: 0.3% Impurity 3: 0.5% RRT 0.90: 0.1% RRT 0.91: 0.1% RRT 0.93: 0.2% RRT 1.04: 0.2% Impurity 4: 0.4% RRT 1.32: 0.1% Total: 4.6% |
| Water content | USP <921> Ia | Measured value | 1.4% | 1.6% | 2.2% | 1.8% | 1.9% |
| Disintegration time | USP <701> | Average of measured values | 1:56, 2:18, 1:58, 1:46, 1:54, 2:29 Average value: 2:04 | 1:50, 2:26, 2:38, 2:02, 1:58, 2:10 Average value: 2:11 | 1:47, 1:56, 1:25, 2:08, 1:37, 2:14 Average value: 1:51 | 2:09, 1:32, 1:38, 1:50, 2:06, 2:13 Average value: 1:55 | 0:59, 1:16, 1:21, 1:28, 1:34, 1:41 Average value: 1:23 |

TABLE 12-1-continued

Stability of capsule preparation of DFP-11207 (100 mg) according to the second prescription in severe conditions (30° C./65% RH)

| | | Specifications | | | | |
|---|---|---|---|---|---|---|
| | | 0 month | 1 month | 2 months | 3 months | 6 months |
| | | | | Analysis date | | |
| Test | Method | | 2020 May 1 | 2020 Jun. 1 | 2020 Jun. 1 | 2020 Oct. 2 |
| Microbial content | USP <61> USP <62> | Total Aerobic Microbial Count (TAMC) ≤ $10^3$ cfu/g Total Combined Yeasts and Molds Count (TYMC) ≤ $10^2$ cfu/g Escherichia coli: Absent | Total Aerobic Microbial Count (TAMC) ≤ 10 cfu/g Total Combined Yeasts and Molds Count (TYMC) ≤ 10 cfu/g Escherichia coli: Absent | | | Total Aerobic Microbial Count (TAMC) ≤ 10 cfu/g Total Combined Yeasts and Molds Count (TYMC) ≤ 10 cfu/g Escherichia coli: Absent |

TABLE 12-2

Stability of capsule preparation of DFP-11207 (100 mg) according to the second prescription in severe conditions (30° C./65% RH)

| Test | Method | Specifications | 9 months Analysis date 2021 Jan. 4 | 12 months |
|---|---|---|---|---|
| Appearance | ATM-1095 | White, grayish-white or cream color | Grayish-white | |
| Purity | ATM-1349 | 90.0-110.0% | 98.4% | |
| Analog | ATM-1349 | Individual related compounds: Measured value ≥0.1% (% area) Total: measured value | Analog 2: 0.6% RRT 0.35: 0.1% Analog 1: 0.3% Impurity 1: 1.1% Impurity 2: 2.9% RRT 0.74: 0.1% RRT 0.81: 0.3% Impurity 3: 0.5% RRT 0.90: 0.1% RRT 0.91: 0.1% RRT 0.93: 0.2% RRT 1.04: 0.3% Impurity 4: 0.4% RRT 1.31: 0.1% Total: 7.1% | |
| Water content | USP <921>1a | Measured value | 1.7% | |
| Disintegration time | USP<701> | Average of measured values | 1: 13, 1:28, 1:36, 1: 46, 1:59, 2:08 Average value: 1:41 | |
| Microbial content | USP <61> USP <62> | Total Aerobic Microbial Count (TAMC) ≤$10^3$ cfu/g Total Combined Yeasts and Molds Count (TYMC) ≤$10^2$ cfu/g Escherichia coli: Absent | | |

The results of a stability test of DFP-11207 bulk drug not encapsulated are shown in Table 13. The stable period of DFP-11207 bulk drug, during which the specifications of the bulk drug are satisfied, in the acceleration conditions (25° C./humidity 60%) was 3 months or less. The stable period of capsule preparation of DFP-11207 according to the first prescription satisfying the specifications of the preparation in the acceleration conditions (25° C./humidity 60%) was 6 months. The stable period of capsule preparation of DFP-11207 according to the second prescription satisfying the specifications of the preparation in the acceleration conditions (25° C./humidity 60%) was 9 months or more. In comparison with these preparations, the bulk drug was unstable.

TABLE 13

Results of stability test of a bulk drug, DFP-11207 in humidity conditions (25° C./60% RH)

| Test item | Specifications | Results (after 3 months) | | Passing status |
|---|---|---|---|---|
| Appearance | Grayish-white to pale yellow | Grayish-white | | Passed |
| Purity (% area) | ≥96.0% | 94.0% | | Not passed |
| Analog (% area) | Individual impurities: ≤1.0% | Relative elution time | % area | Not passed |
| | | 0.30 | 0.27% | |
| | | Analog-1 (RRT 0.42) | 0.18% | |
| | | Impurity 1 (RRT 0.49) | 0.73% | |
| | | Impurity 2 (RRT 0.74) | 2.13% | |
| | | 0.80 | 0.21% | |
| | | Impurity 3 (RRT 0.83) | 0.49% | |
| | | 0.88 | 0.07% | |
| | | 0.89 | 0.05% | |
| | | 0.90 | 0.10% | |
| | | 0.92 | 0.15% | |
| | | 0.93 | 0.13% | |
| | | 0.94 | 0.05% | |
| | | 1.03 | 0.22% | |
| | | Impurity 4 (RRT 1.13) | 0.86% | |
| | | 1.29 | 0.06% | |
| | | 1.30 | 0.09% | |
| | Total impurities: ≤4.0% | 5.8% | | Not passed |
| Water content | ≤0.5% | 0.2% | | Passed |

INDUSTRIAL APPLICABILITY

Since DFP-11207 is sensitive to humidity, it has been considered that DFP-11207 may not be stably stored for a long term at normal temperature and normal humidity; however, long-term stable storage of DFP-11207 was realized by a new technique not known in the technical field. Based on this, it is likely to stably supply a DFP-11207 product to the market of pharmaceuticals via approval of manufacturing and marketing as a pharmaceutical product. Furthermore, the product can be stored for a long term at hospitals for treating cancer patients and problems of transport of the product have been overcome. Moreover, the present invention realized excellent stability that allows cancer patients to store prescribed drugs (one month's drug prescribed by doctors of hospitals in consideration of the conditions of patients) at room temperature (25° C./humidity 50%) or in a refrigerator (5° C.) at homes. Since the present invention can provide an excellent product of DFP-11207, the invention is extremely beneficial for the pharmaceutical industry.

The invention claimed is:

1. A product comprising a capsule preparation for treating cancer, comprising (a) 5-chloro-2-(3-(3-(ethoxymethyl)-5-fluoro-2,6-dioxo-1,2,3,6-tetrahydopy -rimidine-1-carbonyl) benzoyloxy)pyridine-4-yl-2,6-bis(propionyloxy)isonicotinate (DFP-11207) or a pharmaceutically acceptable salt in an amount of 25 to 65 wt %, thereof and (b) a hygroscopic agent comprising microcrystalline cellulose in an amount of 35 to 75 wt % and colloidal silicon dioxide in an amount of 2 to 5 wt %, wherein the capsule preparation is provided in a container together with a drying agent which is separate from the capsule preparation,
wherein an amount of the drying agent is 2 g to 5 g per 100 mL of a volume of the container, and
wherein the DFP-11207 is sensitive to humidity;
wherein the cancer is selected from the group consisting of colorectal cancer, gastric cancer, esophageal cancer, pancreatic cancer, hepatocellular carcinoma, gallbladder cancer, biliary tract cancer, breast cancer, ovarian cancer, endometrial cancer, cervical cancer, head and neck cancer and non-small cell lung cancer; and the drying agent is selected from the group consisting of silica gel, alumina gel, zeolite, alumina, bauxite, anhydrous calcium sulfate, calcium chloride, lithium chloride, magnesium chloride, lime, clay, zeolite, talc, diatomaceous earth, white clay, carbon black, a high water-absorption resin, a synthetic resin powder, a sulfate, a carbonate, a hydroxide, an oxide, a chloride, a phosphate and combinations thereof.

2. The product according to claim 1, which comprises the DFP-11207 or a pharmaceutically acceptable salt thereof in an amount of 100 mg.

3. The product according to claim 1, wherein a coating base for a capsule shell thereof contains hydroxypropyl methylcellulose.

4. The product according to claim 1, which has a capsule size of 2 to 00.

5. A method for producing a product for treating cancer, comprising filling a capsule shell with (a) 5-chloro-2-(3-(3-(ethoxymethyl)-5-fluoro-2,6-dioxo-1,2,3,6-tetrahydopy-rimidine-1-carbonyl)benzoyloxy)pyridine-4-yl-2,6-bis(propionyloxy)isonicotinate (DFP-11207) or a pharmaceutically acceptable salt thereof in an amount of 25 to 65 wt % and (b) a hygroscopic agent comprising microcrystalline cellulose in an amount of 35 to 75 wt % and colloidal silicon dioxide in an amount of 2 to 5 wt %, and
providing the produced capsule preparation in a container together with a drying agent which is separate from the capsule preparation, wherein an amount of the drying agent is 2 g to 5 g per 100 mL of a volume of the container, wherein the DFP-11207 is sensitive to humidity;
wherein the cancer is selected from the group consisting of colorectal cancer, gastric cancer, esophageal cancer, pancreatic cancer, hepatocellular carcinoma, gallbladder cancer, biliary tract cancer, breast cancer, ovarian cancer, endometrial cancer, cervical cancer, head and neck cancer and non-small cell lung cancer;
and the drying agent is selected from the group consisting of silica gel, alumina gel, zeolite, alumina, bauxite, anhydrous calcium sulfate, calcium chloride, lithium chloride, magnesium chloride, lime, clay, zeolite, talc, diatomaceous earth, white clay, carbon black, a high water-absorption resin, a synthetic resin powder, a sulfate, a carbonate, a hydroxide, an oxide, a chloride, a phosphate and combinations thereof.

6. The product according to claim 1, wherein the container contains (a) 50 capsules, each comprising 5-chloro-2-(3-(3-(ethoxymethyl)-5-fluoro-2,6-dioxo-1,2,3,6-tetrahydopy-rimidine-1-carbonyl)benzoyloxy)pyridine-4-yl-2,6-bis(propionyloxy)isonicotinate (DFP-11207) or a pharmaceutically acceptable salt thereof and a hygroscopic agent; and (b) 3 g of silica gel as the drying agent.

7. The product according to claim 1, which comprises the DFP-11207 or a pharmaceutically acceptable salt thereof in an amount of 62.5 wt %, the microcrystalline cellulose in an amount of 35.5 wt % and the colloidal silicon dioxide in an amount of 2 wt % based on weight of the capsule preparation.

8. The product according to claim 1, which comprises the DFP-11207 or a pharmaceutically acceptable salt thereof in an amount of 25 wt %, the microcrystalline cellulose in an amount of 73 wt % and the colloidal silicon dioxide in an amount of 2 wt % based on weight of the capsule preparation.

9. The method according to claim 5, wherein the container contains (a) 50 capsules, each comprising 5-chloro-2-(3-(3-(ethoxymethyl)-5-fluoro-2,6-dioxo-1,2,3,6-tetrahydopy-rimidine-1-carbonyl)benzoyloxy)pyridine-4-yl-2,6-bis(propionyloxy)isonicotinate (DFP-11207) or a pharmaceutically acceptable salt thereof and a hygroscopic agent; and (b) 3 g of silica gel as the drying agent.

10. The method according to claim 5, wherein the DFP-11207 or a pharmaceutically acceptable salt thereof in an amount of 62.5 wt %, and the microcrystalline cellulose in an amount of 35.5 wt % and the colloidal silicon dioxide in an amount of 2 wt % as the hygroscopic agent are provided based on weight of the capsule preparation.

11. The method according to claim 5, wherein the DFP-11207 or a pharmaceutically acceptable salt thereof in an amount of 25 wt %, and the microcrystalline cellulose in an amount of 73 wt % and the colloidal silicon dioxide in an amount of 2 wt % as the hygroscopic agent are provided based on weight of the capsule preparation.

\* \* \* \* \*